United States Patent [19]

Pfirmann

[11] Patent Number: 5,410,082

[45] Date of Patent: Apr. 25, 1995

[54] PROCESS FOR PREPARING AMINES

[76] Inventor: Ralf Pfirmann, Hoechst Aktiengesellschaft, D-65926 Frankfurt am Main, Germany

[21] Appl. No.: 239,279

[22] Filed: May 9, 1994

[30] Foreign Application Priority Data

May 11, 1993 [DE] Germany ............... 43 15 623.1

[51] Int. Cl.$^6$ ........................... C07C 209/50
[52] U.S. Cl. ................... 564/414; 558/418; 560/19; 562/458; 564/1; 564/448; 564/488
[58] Field of Search ............ 564/1, 414, 448, 488; 558/418; 560/19; 562/458

[56] References Cited

U.S. PATENT DOCUMENTS

| | | | |
|---|---|---|---|
| 965,903 | 8/1910 | Hofmann et al. | 564/488 |
| 991,721 | 5/1911 | Hofmann et al. | 564/488 |
| 1,850,526 | 3/1932 | Zitscher | 564/414 X |
| 4,198,348 | 4/1980 | Bertini et al. | 564/414 |
| 5,011,997 | 4/1991 | Hazen et al. | 564/414 X |
| 5,032,687 | 7/1991 | Diehl et al. | 564/1 |

OTHER PUBLICATIONS

The Merck Index, Tenth Edition, (1983), Merck & Co., Inc., Rahway, N.J., p. ONR–45.

Primary Examiner—Richard L. Raymond

[57] ABSTRACT

Process for preparing amines by reacting amides in aqueous-alkaline solutions and/or suspensions with halogens or hypohalites in the presence of alcohols, and converting the reaction products into the amines by hydrolysis, hydrogenation or reductive methods.

20 Claims, No Drawings

1

PROCESS FOR PREPARING AMINES

DESCRIPTION

The present invention relates to a novel process for preparing amines by an advantageous, novel variant of the Hofmann degradation, whereby products which previously it was only possible to make available by means of complicated processes can be obtained simply and in high yields.

The process is used to prepare amines, in particular anilines, from the corresponding aides, in particular the benzamides, with these amines representing important precursors in the preparation of liquid crystals, plant protection agents and pharmaceuticals. For example, 2,6-dihaloanilines, in particular 2,6-difluoroaniline and 2,6-dichloroaniline, can be prepared by the process according to the invention. In addition, it is possible to prepare 4-trifluoromethylaniline, or aliphatic amines, such as, for example, cyclopropylamine. The use of the amines which can be prepared, and the provenance of the starting materials, will be briefly illustrated on the basis of these examples.

2,6-Difluoroaniline is used, for example, as an intermediate in the preparation of pharmaceuticals (EOS 497 564, PCT WO 9115464) and liquid crystals for use in displays (JP 04029976). 2,6-Dichloroaniline can be processed to give highly active pharmaceuticals (EOS 497 564, U.S. Pat. No. 5,130,441, A. Andreani et al., Acta Pharm. Nord., 4 (2), 93–96), inter alia. In addition to its other applications, 4-trifluoromethylaniline is used to prepare anthelmintics (U.S. Pat. No. 5,034,410) and antiinflammatory and immunomodulatory agents (U.S. Pat. No. 5,001,124). The use of cyclopropylamine which is currently the most important is that of preparing fluorinated quinolonecarboxylic acids (DOS 3420789, EOS 275 971), which have gained great importance as antibacterial agents. The precursors which can be prepared in accordance with the invention can be converted into the active substances or the active compounds by the methods given in the cited literature.

2,6-Difluorobenzamide, the starting material for 2,6-difluoroaniline, is obtained from 2,6-difluorobenzonitrile by methods which are well known in the literature (J. March, Advanced Organic Chemistry (1985), 788). For example, it is possible to react 2,6-difluorobenzonitrile with hydrogen peroxide in aqueous-alkaline medium (JP-OS 60-132 942). 2,6-Dichlorobenzamide can be prepared from 2,6-dichlorobenzonitrile in an analogous manner. 4-Trifluoromethylbenzamide can be prepared, for example, from 4-trifluoromethylbenzonitrile (J. X. Wang et al., J. Chem. Res., Synop., (12), 456–457) or from 4-trifluoromethylbenzoic acid (D. E. Walch et al., J. Med. Chem. 12 (1969), 299–303). Several, industrially practicable, routes exist for preparing cyclopropanecarboxamide (EOS 365970, DOS 3026094).

Hofmann degradation reactions, such as those in question, only proceed with moderate yields and selectivities, particularly in the case of amides which are 2,6-disubstituted and/or electron-poor. Under the drastic reaction conditions used in this context, hydrolysis of the amide, ring chlorination and oxidative degradation, in particular by means of oxidation on the nitrogen, frequently occur as side reactions provoked by the high reaction temperatures which are necessary. In some cases, it is necessary to add expensive or toxic auxiliary substances, such as, for example, phase-transfer catalysts (JP 61 271255). In many cases, these negative factors render the preparation of these amines uneconomical.

In the case of 2,6-disubstituted amides, addition of hydroxide to the isocyanate intermediate is not favored for steric reasons, particularly when relatively large substituents are present (Org. React. 3, 277–282 (1946)). As a consequence, hardly any such reactions are known.

Furthermore, hydrolysis of the amide bond to the carboxylate in the starting compound is facilitated (not wanted) by electron-withdrawing substituents, with the rearrangement simultaneously being retarded. Although the rearrangement is favored in the case of electron-donating substituents, such as alkoxy or hydroxyl groups, ring chlorination is then also, disadvantageously, accelerated. (e.g. Haufer et al., J. Am. Chem. Soc. 59, 121 (1937) ibid. 60, 2308 (1937), ibid. 61, 618 (1939)). It is also known that, while raising the temperature favors the rearrangement over unwanted hydrolysis, the strongly oxidizing and halogenating character of the reagent is thereby once again brought to bear. However, this is not advantageous, and not wanted, particularly in the case of oxidation-sensitive amines, in particular in the case of aromatic amines.

The formation of alkylacylureas represents the most frequent side reaction in the case of aliphatic and cycloaliphatic amides.

There was, therefore, a very pressing need for a novel process for preparing amines, which process does not suffer from the described disadvantages, is based on readily available starting materials, makes the desired compounds available in high yield, and, in addition, can be carried out on an industrial scale without great expense.

This object is achieved by a process for preparing amines. In this process, amides are reacted in aqueous-alkaline solutions and/or suspensions with halogens or hypohalites in the presence of alcohols, and the reaction products are converted into the amines by hydrolysis, hydrogenation or reductive methods. Surprisingly, many amides can be converted into the corresponding amines using this novel process. Thus, good results can be obtained with ($C_1$-$C_{10}$)-alkylamides, it being possible for the alkyl radical to be substituted by one to four ($C_1$-$C_4$)-alkyl groups, ($C_1$-$C_4$)-alkoxy groups, fluorine, chlorine or bromine atoms, nitro groups, cyano groups, trifluoromethyl groups, ($C_1$-$C_4$)-alkoxy groups, or benzyloxy groups whose phenyl radical can, in turn, carry one to three ($C_1$-$C_4$)-alkyl groups, ($C_1$-$C_4$)-alkoxy groups, fluorine, chlorine or bromine atoms, nitro groups, cyano groups, trifluoromethyl groups or ($C_1$-$C_4$)-alkoxycarbonyl groups.

In many cases, the process has also proved to be of value for preparing aromatic amines, it being possible for the aromatic radical to be phenyl, naphthyl or heteroaryl, such as, for example, pyridine, thiophene or pyrrole. The aromatic radical can also be substituted by an arbitrary number of chlorine, fluorine or bromine atoms, or trifluoromethyl, nitro, cyano, carboxyl, ($C_1$-$C_4$)-alkoxycarbonyl, ($C_1$-$C_4$)-alkyl or ($C_1$-$C_4$)-alkoxy groups.

The amides are reacted with chlorine, bromine, sodium hypochlorite or sodium hypobromite in aqueous-alkaline medium in the presence of alcohols.

The process can be carried out using hypohalite solutions (bleaching liquors), which is equivalent to metering elemental halogen into solutions having an alkaline effect. An indication of the quantity of halogen employed is sufficient to describe the reaction conditions, since hypohalite solutions are formed in situ when the halogen makes contact with the aqueous solutions having an alkaline effect which are employed. Chlorine or bromine are used, therefore, in quantities of between about 1 mol and about 5 mol, in particular of about 1.01 mol and about 2 mol, particularly preferably of between about 1.02 mol and about 1.2 mol, in each case based on 1 mol of amide to be degraded. The use of chlorine is preferred owing to its superior availability on an industrial scale. The halogen can be added dropwise (bromine) or passed in in the form of a gas (chlorine). Depending on the reaction temperature and size of the batch, suitable metering times in this context are between about 0.5 h and about 16 h, preferably about 1 h and 4 h, with that abovementioned qualification regarding the metering time applying which is determined by the necessary removal of the heat formed during the reaction, which takes place exothermically.

If bleaching liquors, i.e. aqueous hypohalite solutions, are metered in, which, for operative reasons, generally has advantages on a laboratory scale over using elemental halogen, solutions are then used having a content of active chlorine of from about 30 to about 250 g per kg of solution, preferably between about 100 and about 160 g of active chlorine per kg of solution, or from about 60 to about 550 g of active bromine per kg of solution, preferably of between about 200 and 350 g per kg of solution. These solutions can be obtained by metering the corresponding quantities of chlorine or bromine into aqueous solutions having an alkaline effect.

In carrying out the reaction of the Hofmann degradation type, temperatures of between about $-15°$ C. and about 80° C., preferably of between about 0° C. and about 50° C., particularly preferably of between about 10° C. and about 40° C., are customarily employed.

These low temperatures are particularly advantageous since, as a result of the low temperature, the oxidative effect of the chlorine, which in conventional processes leads to many by-products, is markedly diminished.

In accordance with the invention, the degradation of the amides to the amines is carried out in the presence of alcohols. In this context, ($C_1$-$C_8$)-alkanols of any structure, which additionally can be substituted by alkoxy-($C_1$-$C_4$) groups, fluorine, chlorine or bromine atoms, nitro groups, cyano groups, trifluoromethyl groups or alkoxy($C_1$-$C_4$)-carbonyl groups, may be used as alcohols, as may phenylmethanols, where the phenyl radical can be substituted by alkyl($C_1$-$C_4$) groups, alkoxy($C_1$-$C_4$) groups, fluorine, chlorine or bromine atoms, nitro groups, cyano groups, trifluoromethyl groups or alkoxy($C_1$-$C_4$)-carbonyl groups. Primary alcohols, in particular methanol, ethanol and benzyl alcohol, are particularly suitable.

In many cases, it has proved of value to employ the alcohols in quantities of from 1 to 20 mol, in particular of from 1.1 to 10 mol, preferably of from 1.05 to 5 mol, per mol of amide.

The alcohols are employed in mixtures together with solutions or suspensions having an alkaline effect. The latter can be prepared from alkali metal or alkaline earth metal compounds. Such compounds having an alkaline effect are, for example, hydroxides, carbonates, hydrogen carbonates, phosphates, hydrogen phosphates, dihydrogen phosphates or oxides, or similar compounds or mixtures thereof, in particular the corresponding alkali metal compounds, preferably sodiumhydroxide, potassiumhydroxide, sodium carbonate and/or potassium carbonate. The compounds having an alkaline effect are used in quantities, based on amide to be degraded, of between about 1 mol and about 30 mol, preferably of between about 3 mol and about 15 mol, particularly preferably of between about 5 mol and about 10 mol. The concentrations of the aqueous solutions depend on the amide employed, but typically amount to between about 1 mol/l and about 20 mol/l, preferably to between 3 mol/l and 10 mol/l. In practice, the quantity of the aqueous suspension having an alkaline effect is chosen such that it is still possible to stir the reaction mixture without difficulty. The reaction times amount to from about 0.5 h to about 16 h, depending on the speed of metering-in, which, owing to the nature of the reactions, can depend on the cooling surfaces available. The primary reaction product of the reaction according to the invention, proceeding in the sense of a Hofmann degradation, is presumably an alkyl carbamate of the desired amine, since the isocyanate arising as an intermediate is probably captured by the alcohols, which are nucleophilic under the reaction conditions. As a consequence, the oxidation-sensitive amines are, surprisingly, withdrawn from the oxidizing effect of the halogens, and it is thus possible only to release the amines, in a deliberate manner by hydrolysis, hydrogenation or generally through reduction, after the rearrangement step.

It is known to obtain amines, in particular anilines, from carbamates. (T. W. Greene, P. G. M. Wuts, Protective Groups in Organic Chemistry (1991), 317–348). In the present case, the elimination of the amino group is achieved simply by heating the reaction mixture according to the invention, after any chlorine or bromine excess which may be present has been destroyed. Optionally substituted benzyl carbamates can be hydrolyzed under alkaline conditions at from 80° to 100° C. in less than 10 h, whereas simple alkyl carbamates require reaction times of up to 96 h at the same temperatures.

In general, the reaction products can be isolated simply by phase separation, resulting in mixtures with the alcohols employed. The phase separation can be improved or induced by adding additional solvents, such as, for example, toluene or xylene. The alcohol which has been eliminated can, where appropriate after having been separated off and purified, be reintroduced into the process according to the invention.

The use of optionally substituted benzyl alcohol is particularly convenient, since the corresponding benzyl carbamates can also be cleaved by hydrogenation relatively simply and therefore cost-effectively. (T. W. Greene et al., loc. cit., 335–341).

Hydrogenation using hydrogen gas in the presence of transition metal catalysts, in particular of palladium on active charcoal, turns out to be particularly simple. Apart from palladium, nickel or platinumare particularly suitable for employment as transition metals. The hydrogenations proceed smoothly under a hydrogen pressure of between about 1.1 bar and about 100 bar, and at temperatures of between about 10° C. and about 80° C., in lower aliphatic alcohols or simple aromatic or aliphatic hydrocarbons, such as, for example, hexane, methylcyclohexane, toluene, xylene, methanol, butanol, isopropanol or ethanol as solvents, or mixtures thereof. The precious metal catalysts are employed in quantities of between about 0.05 and about 3, preferably about 0.3 to 1, % by weight (calculated as pure transition metal).

An alternative possibility is the use of so-called transfer hydrogenation to synthesize the novel intermediates (T. W. Greene et al., loc. cit., 156-160).

Typically, the concentration of the end product in the hydrogenation mother liquor is between about 10 and 500, preferably between about 100 and 300, g/l. If the products obtained by reaction with unsubstituted benzyl alcohol are employed, toluene is then obtained in the hydrogenation in addition to the desired amine. For this reason, toluene is preferred as the solvent for the hydrogenation. In general, the end product can be isolated by evaporating down the solutions which have been filtered from the catalyst, if necessary when hot, and subsequently filtering. In this context, it may be appropriate to carry out the work in the presence of oxidation-preventing additives, such as, for example, hydrazine or hydrazinium salts or 2,6-di-tert-butyl-4-methylphenol, since the anilines prepared by the process according to the invention, in particular, are, as end products, highly labile towards atmospheric oxygen, particularly on heating.

In addition to hydrolysis and hydrogenation, methods which are generally reductive can also be used for liberating the amine. Reductive methods are understood to mean reaction of the reaction product with organoaluminum hydrides, boron hydrides, silicon hydrides, metals and/or hydrazine.

The desired novel product of value can be obtained by the customary isolation and purification methods in dependence on the properties of the material (state of aggregation, solubility behavior). In the case of liquid products, simple phase separation, which can be improved by adding solvents, is particularly suitable. Many of the amines to be prepared are steam-volatile, so that steam distillation represents a method of separating off the product from the reaction mixture which is both mild and easy to put into effect on an industrial scale. Solid products can be isolated by filtration or extraction and subsequently purified by crystallization. Both distillation and chromatography can be used for purifying liquid and solid products; as a rule, liquid products are fractionated.

In a particularly preferred embodiment of the process, 2,6-difluorobenzamide is reacted to give 2,6-difluoroaniline.

The following examples elucidate the process without limiting it.

EXAMPLE 1

180 g of benzyl alcohol and 269 g (6.725 mol) of sodium hydroxide are introduced into 450 g of water. 220 g (0.9 mol) of 2-benzyloxy-6-fluorobenzamide are added at 20° C., and chlorine is passed in (15 l/h), while stirring thoroughly, at 40° C. The reaction is monitored by gas chromatography and terminated after 2.5 h, when transformation is complete.

At this point, 2-benzyloxy-6-fluoroaniline can be isolated, by extracting with methyl tert-butyl ether (MTBE), drying over magnesium sulfate and removing the solvent, as a pale-brown colored, viscous oil, provided that, after destroying excess chlorine, the mixture is heated at 95° C. for 3 h (see Example 3 as well; however this step is omitted here).

Procedure a

The aqueous mother liquor is heated at 95° C. for 3 h, once any excess chlorine has been destroyed by adding sodium sulfite. The organic phase is separated from the aqueous phase, taken up in 200 ml of methanol and, after that, stirred vigorously (15 h) together with 5 g of Pd/C (5% Pd, 50% moist) under an $H_2$ atmosphere (slight excess pressure) until compounds possessing benzyloxy groupings can no longer be detected. The catalyst is filtered off and then washed with methanol. Most of the methanol is distilled off under an inert gas and 300 g of toluene are added. After cooling (0° C.), 60.9 g (0.48 mol, 53%) of 2-amino-3-fluorophenol, which is colored pale brown to dark gray, are obtained after drying (content (GC): 100%). A further 24.2 g (0.19 mol, 21%) of product are contained in the black mother liquor, as is demonstrated by quantitative gas chromatography. The mother liquor is reused for further batches.

Procedure b

After some minutes without stirring, the phases are separated and 300 g of methanol are added to the organic phase and this latter mixture is then stirred vigorously (20 h) together with 5 g of Pd/C (5% Pd, 50% moist) under an $H_2$ atmosphere (slight excess pressure). The GC analysis reveals solvent and, apart from minor quantities of by-products, 2-amino-3-fluorophenol as the main component. The catalyst is filtered off and then washed with methanol. Under an inert gas, most of the methanol is distilled off from the filtrate and 300 g of toluene are added. After cooling (0° C.), and after drying, 65.3 g (0.51 mol, 57%) are obtained of 2-amino-3-fluorophenol, which is of a pale brown color. (Content (GC): 100%). A further 28.2 g (0.22 mol, 25%) of product are contained in the mother liquor, as is determined by quantitative gas chromatography. The mother liquor is reused for further batches.

EXAMPLE 2

60 g (1.5 mol) of sodium hydroxide, 40 g (0.37 mol) of benzyl alcohol and 25.8 g (0.164 mol) of 2,6-difluorobenzamide are initially introduced in 140 g of water. A stream of chlorine of 5 l/h is passed into this suspension at 20°–30° C. (moderate exothermy). After 1 h, the reaction is concluded, the metering-in of chlorine is terminated, and steam is passed, at 100° C., into the solution, which at this stage is clear and orange-colored. After 6 h, 2,6-difluoroaniline is no longer passing over, the two phases of the mother liquor are separated, and extraction of the aqueous phase (MTBE) only yields negligible quantities of additional 2,6-difluoroaniline. The organic phases are combined (88.2 g), and quantitative analysis revealed a 2,6-difluoroaniline content of 19.4 g (0.15 mol, 92%). The product can be obtained in pure form by fractionation (atmospheric pressure).

EXAMPLE 3

120 g of methanol, 70 g of water, 30 g (0.75 mol) of sodium hydroxide and 24.5 g (0.1 mol) of 2-benzyloxy-6-fluorobenzamide are initially introduced and heated to 40° C. Chlorine is passed in (4 l/h), the initially colorless suspension assuming a brownish color after a short while, and it being possible to switch off the heating since the temperature is maintained owing to the reaction being exothermic. After 25 min, the reaction is concluded, as can be demonstrated by GC. A clear solution is obtained in place of the suspension which was present initially. The methanol is distilled off under a weak vacuum (50° C.), and the resulting suspension of 2-benzyloxy-6-fluoro-N-carboxymethoxyaniline is heated at 100° C. for 48 h. After the mixture has been cooled, 50 g of toluene are added, the phases are separated, and 2 g of $MgSO_4$ and 1 g of active charcoal are added to the organic phase, which is stirred for some hours. After filtration and removal of solvent on a rotary evaporator, 19.8 g (91 mmol, 91%) of 2-benzyloxy-6-fluoroaniline are obtained as a brownish, clear oil, which is of excellent purity (GC: >96%) for further reactions.

2-Benzyloxy-6-fluoro-N-carbomethoxyaniline can be isolated by following the procedure already indicated in Example 1 but omitting the 48-hour hydrolysis of the intermediate, which is isolated and purified by customary methods (in particular filtration and recrystallization).

EXAMPLE 4

(Comparative Example in Accordance with Methods Known from the Literature)

110 g of water, 109.4 g (1.368 mol) of 50% sodiumhydroxide solution and 86.4 g (0.547 mol) of 2,6-difluorobenzamide are initially introduced, and 262.5 g (0.602 mol) of 17% sodium hypochlorite solution are then metered in at 65° C. over a period of 1 h. It is possible to switch off the heating owing to the exothermic nature of the reaction. After a further 30 min at 70° C., the mixture is heated to 100° C. and steam is passed in. Once no further product passes over, the organic phase in the distillate is separated off, the aqueous phase is subsequently extracted with n-hexane (30 g), and the combined organic phases, which have been dried over magnesium sulfate, are distilled at atmospheric pressure by way of a short Vigreux column. 33.5 g (0.26 mol, 47%) of 2,6-difluoroaniline pass over, at 154°–156° C., as a pale yellowish liquid.

EXAMPLE 5

190.0 g (1 mol) of 2,6-dichlorobenzamide are mixed together with 336.7 g (6 mol) of potassium hydroxide in 1000 g of water and 250 g of ethanol, and the suspension is heated to 50° C. Chlorine is then passed in (6 l/h) at 55° C. for 4 h, excess halogen is then destroyed with sodium sulfite, and thereafter the mixture is heated at 99° C. for 36 h. After that, steam is passed into the mixture at 100° C. and the product is distilled off. The distillates are stirred in the cold at 0°–10° C., and 2,6-dichloroaniline is subsequently filtered off with suction. After drying, 147.3 g (0.909 mol, 91%) of 2,6-dichloroaniline are obtained as a colorless solid.

EXAMPLE 6

189.1 g (1 mol) of 4-trifluoromethylbenzamide and 108 g (1 mol) of benzyl alcohol are introduced into a suspension of 296.4 g (4 mol) of calcium hydroxide and 80 g of sodium hydroxide in 800 g of water, and 520 g (1.04 mol) of 14.8% sodium hypochlorite solution are subsequently metered in at 20° C. within the space of 6 h. The mixture is subsequently stirred at 35° C. for 6 h, and 50 g of toluene are then added to the solution at 20° C. The phases are separated, and 300 g of methanol are added to the organic phase. The mixture is hydrogenated under slight hydrogen pressure at 40° C. for 20 h, while stirring vigorously, using 3 g of palladium on active charcoal (5% Pd, 50% moist). The catalyst is filtered off from the remaining mixture and the solvents are distilled over. The remaining residue is distilled; pale yellowish 4-trifluoromethylaniline passes over at 12 Torr/81°–86° C. 129.1 (0.801 mol, 80%) of trifluoromethylaniline are obtained.

EXAMPLE 7

8.5 g (0.1 mol) of cyclopropanecarboxamide are introduced, at 10° C., into 150 g of 30% sodium hydroxide solution to which 20 g of benzyl alcohol have been added. 17.6 g (0.11 mol) of bromine are added dropwise at this temperature within 30 min. Subsequently, the mixture is heated at 40° C. for 1 h in order to complete the reaction, and excess bromine is destroyed using sodium sulfite. After that, the mixture is boiled for 10 h on a water separator, after which no further cyclopropylemine passes over. The phases are separated, and this is followed by drying with a little magnesium sulfate, and 4.8 g (84 mmol, 84%) of cyclopropylamine are distilled in a microdistillation apparatus at 48°–51° C.

EXAMPLE 8

261.2 g (1.66 mol) of 2,6-difluorobenzamide are suspended in 232.3 g (2.15 mol) of benzyl alcohol, the suspension is heated to 55° C., and 233.3 g (2.08 mol) of 50% potassium hydroxide solution are added dropwise within the space of 2 h. After this time, the temperature is increased to 60° C., and stirring is continued for a further 3 h. Subsequently, a further 600 g of water, 280 g (7 mol) of sodium hydroxide and 185 g (1.71 mol) of benzyl alcohol are added at 10° C., and chlorine is passed in (15–18 l/h) at 40° C. for 3 h. The phases are separated, 500 ml of methanol and 7 g of Pd/C (5% Pd, 50% moist) are added to the organic phase and hydrogenation is carried out as described in Example 1b. After working up in analogy with Example 1b, 123.5 g (0.97 mol, 59%) of 2-amino-3-fluorophenol are obtained as pale-gray shiny flakes.

EXAMPLE 9

2-Amino-3-Fluorophenol Prepared from 2,6-Difluorobenzonitrile in a One-pot Process 69.9 g (0.5 mol) of 2,6-difluorobenzonitrile and 237 g (1.2 mol) of 6-normal sodium hydroxide solution are initially introduced in 200 ml of benzyl alcohol. 221 g (1.95 mol) of 30% hydrogen peroxide solution are added dropwise to this mixture within the space of 30 min, the temperature rising from 20° C., at the beginning of the metering-in, to 50° C., and then being maintained at this value. After 5 h (complete transformation to 2-benzyloxy-6-fluorobenzamide can be demonstrated by GC), the mixture is cooled and supplemented with 200 g of water and 60 g (1.5 mol) of sodium hydroxide. Chlorine is passed in (8–10 l/h) at 30° C. for 2 h, with the reaction being monitored by gas chromatography and terminated once the amide has disappeared. The phases are separated, 180 g of methanol are added to the organic phase, and further processing is carried out as indicated in Example 8. 32.4 g (0.255 mol, 51%) of 2-amino-3-fluorophenol are obtained as a brown-black powder.

I claim:

1. A process for preparing an amine, comprising: reacting an amide in an aqueous-alkaline medium with a halogen or a hypohalite in the presence of an alcohol, and converting the resulting reaction product into the amine by hydrolysis, hydrogenation or reduction.

2. The process as claimed in claim 1, wherein the amide is a ($C_1$–$C_{10}$)-alkylamide whose alkyl radical can be substituted by one to four ($C_1$–$C_4$)-alkyl groups, fluorine, chlorine or bromine atoms, nitro groups, cyano groups, trifluoromethyl groups, ($C_1$–$C_4$)-alkoxy groups, or benzyloxy groups whose phenyl radical can, in turn, carry one to three ($C_1$–$C_4$)-alkyl groups, ($C_1$–$C_4$)-alkoxy groups, fluorine, chlorine or bromine atoms, nitro groups, cyano groups, trifluoromethyl groups or ($C_1$–$C_4$)-alkoxycarbonyl groups.

3. The process as claimed in claim 1, wherein the amide is an aromatic amide.

4. The process as claimed in claim 3, wherein the aromatic radical of said aromatic amide is phenyl, naphthyl or heteroaryl which is optionally substituted by an arbitrary number of chlorine, fluorine or bromine atoms, or trifluoromethyl, nitro, cyano, carboxyl, ($C_1$–$C_4$)-alkoxycarbonyl, ($C_1$–$C_4$)-alkyl or ($C_1$–$C_4$)-alkoxy groups.

5. The process as claimed in claim 1, wherein the amide is reacted with halogen by reacting the amide in an aqueous-alkaline medium containing chlorine, bromine, sodium hypochlorite or sodium hypobromite in a quantity of from 1 to 5 mol, per mol of amide.

6. The process as claimed in claim 5, wherein active chlorine is reacted with the amide in a quantity of from 30 to 250 g, or active bromine is reacted with the amide in a quantity of from 60 to 550 g, per kg of aqueous-alkaline medium.

7. The process as claimed in claim 1, wherein the amide is reacted at a temperature in the range of from −15° C. to 80° C.

8. The process as claimed in claim 1, wherein a said alcohol is a ($C_1$–$C_8$)-alkanol, which can be substituted by one to three ($C_1$–$C_4$)-alkoxy groups, fluorine, chlorine or bromine atoms, nitro groups, cyano groups, trifluoromethyl groups or ($C_1$–$C_4$)-alkoxy-carbonyl groups.

9. The process as claimed in claim 1, wherein a said alcohol is a benzyl alcohol, whose phenyl radical can be substituted by one to three ($C_1$–$C_4$)-alkyl groups, ($C_1$–$C_4$)-alkoxy groups, fluorine, chlorine or bromine atoms, nitro groups, cyano groups, trifluoromethyl groups or ($C_1$–$C_4$)-alkoxycarbonyl groups.

10. The process as claimed in claim 1, wherein a said alcohol is present in an amount of from 1 to 20 mol, per mol of amide.

11. The process as claimed in claim 1, wherein a said aqueous-alkaline medium is an aqueous solution and/or suspension of alkali metal or alkaline earth metal hydroxide, carbonate, hydrogen carbonate, phosphate, hydrogen phosphate, dihydrogen phosphate or oxide, or a mixture of these compounds.

12. The process as claimed in claim 1, wherein the amide is 2,6-difluorobenzamide, which amide is converted into 2,6-difluoroaniline.

13. The process as claimed in claim 5, wherein said quantity ranges from 1.01 to 2 mol, per mol of amide.

14. The process as claimed in claim 5, wherein said quantity ranges from 1.02 to 1.2 mol, per mol of amide.

15. The process as claimed in claim 7, wherein said temperature is in the range of from 0° C. to 50° C.

16. The process as claimed in claim 7, wherein said temperature is in the range of from 10° C. to 40° C.

17. The process as claimed in claim 6, wherein said amount of active chlorine ranges from 100 to 160 g and said amount of active bromine ranges from 200 to 350 g, per kg of said aqueous-alkaline medium.

18. The process as claimed in claim 8, wherein the ($C_1$–$C_8$)-alkanol is methanol or ethanol.

19. The process as claimed in claim 10, wherein a said alcohol is present in an amount of from 1.05 to 5 mol per mol of amide.

20. The process as claimed in claim 11, wherein the alkaline earth metal hydroxide is sodium hydroxide or potassium hydroxide.

* * * * *